United States Patent [19]

Gaffar

[11] 4,339,431
[45] Jul. 13, 1982

[54] ANTICALCULUS ORAL COMPOSITION

[75] Inventor: Abdul Gaffar, Somerset, N.J.

[73] Assignee: Colgate-Palmolive Company, New York, N.Y.

[21] Appl. No.: 221,665

[22] Filed: Dec. 31, 1980

[51] Int. Cl.³ .......................... A61K 7/16; A61K 7/22
[52] U.S. Cl. ........................................ 424/54; 424/49
[58] Field of Search ................... 424/49, 54; 528/328

[56] References Cited

U.S. PATENT DOCUMENTS

| | | | |
|---|---|---|---|
| 2,705,705 | 4/1955 | Chirtel et al. | 528/328 |
| 2,904,538 | 9/1959 | Gaertner et al. | 528/328 X |
| 3,929,988 | 12/1975 | Barth | 424/54 |
| 3,932,605 | 1/1976 | Vit | 424/54 |
| 3,939,261 | 2/1976 | Barth | 424/49 |
| 3,943,241 | 3/1976 | Anderson et al. | 424/54 |
| 4,041,149 | 8/1977 | Gaffar et al. | 424/57 |
| 4,110,429 | 8/1978 | Gaffar et al. | 424/54 |
| 4,154,813 | 5/1979 | Kleinberg | 424/54 |
| 4,225,579 | 9/1980 | Kleinberg | 424/54 |
| 4,256,731 | 3/1981 | Curtis et al. | 424/54 |
| 4,269,822 | 5/1981 | Pellico et al. | 424/54 |
| 4,277,464 | 7/1981 | Reussner et al. | 424/54 |

FOREIGN PATENT DOCUMENTS

| | | |
|---|---|---|
| 1943971 | 5/1971 | Fed. Rep. of Germany . |
| 2187288 | 2/1974 | France . |
| 49-09743 | 3/1974 | Japan . |
| 52-110836 | 9/1977 | Japan . |
| 55-69505 | 5/1980 | Japan . |
| 56-08310 | 1/1981 | Japan . |

OTHER PUBLICATIONS

Chase et al., "Immunochemistry", vol. 2, pp. 168–169, (1978), Academic Press.

Primary Examiner—Shep K. Rose
Attorney, Agent, or Firm—Herbert S. Sylvester; Murray M. Grill; Robert L. Stone

[57] ABSTRACT

An oral composition is disclosed containing an effective auticalculus amount of a copolymer of glutamic acid, tyrosine and optionally alanine.

8 Claims, No Drawings

ANTICALCULUS ORAL COMPOSITION

This invention relates to oral compositions containing an anticalculus agent.

Calculus is a hard, mineralized formation which forms on the teeth. Regular brushing prevents a rapid build-up of these deposits, but even regular brushing is not sufficient to remove all of the calculus deposits which adhere to the teeth. Calculus is formed on the teeth when crystals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline hydroxyapatite is an amorphous or microcrystalline calcium phosphate. "Amorphous calcium phosphate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristic of all crystalline materials, including hydroxyapatite. It is apparent therefore that agents which effectively interfere with crystalline growth of hydroxyapatite will be effective as anticalculus agents. A suggested mechanism by which the anticalculus agents of this invention inhibit calculus formation probably involves an increase of the activation energy barrier thus inhibiting the transformation of precursor amorphous calcium phosphate to hydroxyapatite.

Studies have shown that there is a good correlation between the ability of a compound to prevent hydroxyapatite crystalline growth in vitro and its ability to prevent calcification in vivo.

A substantial number of different types of compounds and compositions have been developed for use as antibacterial, and antiplaque and anticalculus agents in oral compositions, including for example such cationic materials as the bisbiguanide compounds and quaternary ammonium compounds, e.g. benzethonium chloride and cetyl pyridinium chloride, disclosed in U.S. Pat. No. 4,110,429. These cationic materials however tend to stain the teeth with continued use. Further, they exert an antibacterial function which undesirably tends to disrupt or destroy the normal microflora of the mouth and/or the digestive system. Other such materials have been found to be unstable in the presence of anionic surface active agents often present in conventional oral compositions.

It is an object of this invention to provide an oral anticalculus composition which will not be subject to one or more of the above deficiencies.

It is another object of this invention to provide an improved anticalculus oral composition which will have relatively little or no tendency to stain the teeth.

A further object of the invention is to provide an oral composition which inhibits the transformation of amorphous calcium phosphate to hydroxyapatite crystal structure normally associated with calculus.

Another object of this invention is the provision of an improved method for inhibiting the formation of calculus.

Other objects and advantages will appear as the description proceeds.

In accordance with certain of its aspects, this invention relates to an oral composition comprising an orally acceptable vehicle containing in an effective amount as an anticalculus agent a copolymer consisting essentially of:

(a) n units having the molecular configuration of units derived from glutamicacid, (b) m units having the molecular configuration of units derived from alanine, and (c) p units having the molecular configuration of units derived from tyrosine, the ratio of (n+m):p ranging from about 5:1 to about 9.5:1 and the ratio of m:n ranging from 0:1 to about 0.6:1, the molecular weight of the copolymer ranging from about 5,000 to about 150,000.

The afore-mentioned copolymers may be prepared in well known manner, as for example by the procedure disclosed in Chase and Williams "Immunochemistry", Vol. 2, pp 168, 169 (1978) Academic Press. In general, the copolymers are prepared by random copolymerization of the N-carboxyanhydrides of glutamic acid, tyrosine and alanine in the required molar proportions in the form of a mixture in an organic solvent such as dioxane, benzene, dimethyl formamide or N-methyl pyrrolidone and in the presence of an initiator such as an organic amine (e.g. triethylamine) or sodium methoxide.

The (A) units in the copolymer may be depicted as having the structural formula:

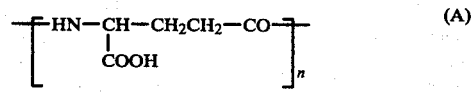

(A)

n being a numerical value representing the number of (A) units of glutamic acid in the copolymer.

The (B) units in the copolymer may be depicted as having the structural formula:

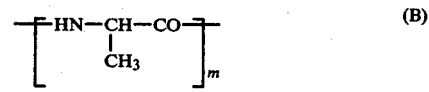

(B)

m being a numerical value representing the number of (B) units of alanine in the copolymer.

The (C) units in the copolymer may be depicted as having the structural formula:

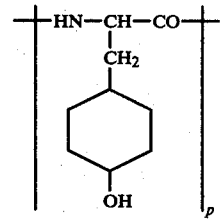

p being a numerical value representing the number of (C) units of tyrosine in the copolymer.

As defined above, the ratio of (n+m):p ranges from about 5:1 to about 9.5:1, the ratio of m:n ranges up to about 0.6:1 and the values of m, n and p are such that the copolymer has a molecular weight of about 5,000 to about 150,000, preferably about 17,000 to about 100,000.

Especially preferred copolymers are a two component copolymer containing glutamic (A) units and tyrosine (B) units in a ratio of about 9:1 and having a molecular weight of about 17,000 to about 21,000, and a three component copolymer containing glutamic (A) units, alanine (B) units and tyrosine (C) units in a ratio of about 6:3:1 and having a molecular weight of about 80,000 to about 100,000.

It will be understood that the free acid form of the copolymers employed herein may be converted to, and employed, in their equivalent salt form by treatment with any base containing an orally acceptable cation such as alkali metal (e.g. sodium or potassium), ammonium, $C_{1-18}$ mono-, di- or tri-substituted ammonium (e.g. alkanol substituted such as mono-, di- or tri-ethanolammonium), organic amines, etc. It will also be understood that when referring to these copolymers as being water soluble such copolymers should be water soluble or readily water dispersible in the concentrations employed in conventional oral compositions such as mouthwashes, toothpastes and the like.

The copolymers employed in accordance with this invention are peculiarly advantageous oral anticalculus agents. Bearing in mind that human saliva contains natural inhibitors of calcium and phosphate precipitation including glutamic acid and tyrosine, the instant copolymers are relatively safe to use even if ingested since they are readily hydrolyzed in the stomach by chymotyprin, a proteolytic enzyme known to hydrolyze tyrosine. In contrast, other non-hydrolyzable anticalculus agents when absorbed in the G.I. tract could cause changes in the bone. These copolymers are additionally advantageous in being substantive to oral surfaces.

The concentration of these copolymer anticalculus agents in oral compositions can range widely, typically upwards of about 0.01% weight with no upper limit except as dictated by cost or incompatibility with the vehicle. Generally, concentrations of about 0.01% to about 10.0%, preferably about 0.1% to about 8.0%, more preferably about 0.5% to about 5.0% by weight are utilized. Oral compositions which in the ordinary course of usage could be accidentally ingested preferably contain concentrations in the lower portions of the foregoing ranges.

In certain highly preferred forms of the invention the oral composition may be substantially liquid in character, such as a mouthwash or rinse. In such a preparation the vehicle is typically a water-alcohol mixture desirably including a humectant as described below. Generally, the ratio of water to alcohol is in the range of from about 1:1 to about 20:1, preferably about 3:1 to 10:1 and most preferably about 4:1 to about 5:1 by weight. The total amount of water-alcohol mixture in this type of preparation is typically in the range of from about 70% to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a lower pH without substantially decalcifying dental enamel. The pH can be controlled with acid (e.g. citric acid or benzoic acid) or base (e.g. sodium hydroxide) or buffered (as with phosphate buffers). Such liquid oral preparations may also contain a surface active agent and/or a fluorine-providing compound.

In certain other desirable forms of this invention, the oral composition may be substantially solid or pasty in character such as toothpowder, a dental tablet, a toothpaste or dental cream. The vehicle of such solid or pasty oral preparations generally contains polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminum silicate, zirconium silicate, silica, bentonite, and mixtures thereof. Preferred polishing materials include Dical*, colloidal silica, silica gel, complex amorphous alkali metal aluminosilicate and hydrated alumina.

*Calcium dihydrogen phosphate

Alumina, particularly the hydrated alumina sold by Alcoa as C333, which has an alumina content of 64.9% by weight, a silica content of 0.008%, a ferric oxide content of 0.003%, and a moisture content of 0.37%, at 110° C., and which has a specific gravity of 2.42 and a particle size such that 100% of the particles are less than 50 microns and 84% of the particles are less than 20 microns, is very effective.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner, as illustrated by Thorpe's Dictionary of Applied Chemistry, Volume 9, 4th Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than about 37 microns.

The polishing material is generally present in amounts ranging from about 10% to about 99% by weight of the oral preparation. Preferably, it is present in amounts ranging from about 10% to about 75% in toothpaste, and from about 70% to about 99% in toothpowder.

In the preparation of toothpowders, it is usually sufficient to admix mecanically, e.g., by milling, the various solid ingredients in appropriate quantities and particle sizes.

In pasty oral preparations the copolymer should be compatible with the other components of the preparation. Thus, in a toothpaste, the liquid vehicle may comprise water and humectant typically in an amount ranging from about 10% to about 90% by weight of the preparation. Glycerine, propylene glycol, sorbitol, or polyethylene glycol 400 may also be present as humectants or binders. Particularly advantageous liquid ingredients comprise mixtures of water, glycerine and sorbitol.

In clear gels where the refractive index is an important consideration, about 3-30% by weight of water, 0 to about 80% by weight of glycerine, and about 20-80% by weight of sorbitol is preferably employed. A gelling agent, such as natural or synthetic gums or gum-like materials, typically Irish moss, sodium carboxymethylcellulose, methyl cellulose, or hydroxyethyl cellulose, may be employed. Other gelling agents which may be employed include gum tragacanth, polyvinylpyrrolidone and starch. They are usually present in toothpaste in an amount up to about 10% by weight, preferably in the range of from about 0.5% to about 5%. The preferred gelling agents are methyl cellulose and hydroxyethyl cellulose. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0, may also contain a surface active agent and/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum, lined lead or plastic, or other squeeze dispenser for metering out the contents, having a label describing it, in substance, as a toothpaste or dental cream.

The oral compositions of this invention may contain a non-soap synthetic sufficiently water soluble organic anionic or nonionic surfactant in concentrations generally ranging from about 0.05 to about 10, preferably about 0.5 to about 5, weight percent, to promote wetting, detersive and foaming properties. U.S. Pat. No. 4,041,149 discloses such suitable anionic surfactants in col. 4, lines 31-38, and such suitable nonionic surfactants in col. 8, lines 30-68 and col. 9, lines 1-12, which passages are incorporated herein by reference thereto.

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, Ca fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as toothpaste or toothpowder, an amount of such compound which releases a maximum of about 1% by weight of the preparation, is considered satisfactory. Any suitable minimum amount of such compound may be used, but it is preferably to employ sufficient compound to release about 0.005% to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013% to 0.1% and most preferably about 0.0013% to 0.5%, by weight, of fluoride ion.

Various other materials may be incorporated in the oral preparations of this invention such as whitening agents, preservatives, silicones, chlorophyll compounds, other anticalculus agents, antibacterial antiplaque agents, and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring or sweetening material may also be employed. Examples of suitable flavoring constituents are flavoring oils, e.g., oils of spearmint, peppermint, wintergreen, sassafras, clove, sage, eucalyptus, majoram, cinnamon, lemon, and orange, and methyl salicylate. Suitable sweetening agents include sucrose, lactose, fructose, maltose, sorbitol, xylitol, sodium cyclamate, perillartine, APM (aspartyl phenyl alanine, methyl ester), saccharin and the like. Suitably, flavor and sweetening agents may together comprise from about 0.01% to 5% or more of the preparation.

In the practice of this invention an oral composition according to this invention such as a mouthwash or toothpaste containing the defined copolymer in an amount effective to inhibit calculus on dental surfaces is applied regularly to dental enamel, preferably from about 5 times per week to about 3 times daily, at a pH of about 4.5 to about 9, generally about 5.5 to about 8, preferably about 6 to 8.

The following examples are further illustrative of the nature of the present invention, but it is understood that the invention is not limited thereto. All amounts and proportions referred to herein and in the appended claims are by weight unless otherwise indicated.

EXAMPLE 1

Inhibition of Crystal Growth of HAP

This is evaluated by a pH Stat method. 1.0 ml of an aqueous solution of $1 \times 10^{-4}$ M to $1 \times 10^{-5}$ M of the anticalculus agent being tested and 0.1 M sodium dihydrogen phosphate is placed in a reaction flask with 22 to 23 ml. of distilled water with continuous stirring in an atmosphere of nitrogen. To this is added 1 ml. of 0.1 M CaCl$_2$ and the pH adjusted to 7.4±0.05 with NaOH (final conc. of Ca$^{++}$ and PO$_4^{3-}$ =4×10$^{-3}$ M). Consumption of 0.1 N NaOH is recorded automatically by a pH Stat (Radiometer). In this test, the formation of HAP occurs in 2 distinct phases. First rapid base consumption (1–4 min.) then diminishes until 15–20 minutes when second rapid uptake takes place. A delay in the time of second rapid consumption or a total absence of the second rapid consumption indicates an interference with the crystal growth of HAP. Agents which interfere with HAP crystal growth are effective anticalculus agents. When tested by the foregoing procedure, the following results are obtained.

TABLE I

| Anticalculus Agent (conc.) | Time (Min.) for HAP Formation | Delay (Min.) for HAP Formation |
|---|---|---|
| (a) Water (Control) | 21.0 | — |
| (b) copolymer 9/1 (20 p.p.m.) | 30.0 | 9.0 |
| (c) copolymer 9/1 (21 p.p.m.) | 40.0 | 19.0 |
| (d) copolymer 9/1 (27 p.p.m.) | 87.0 | 66.0 |
| (e) copolymer 9/1 (32 p.p.m.) | 117.0 | 96.0 |
| (f) Copolymer 6/3/1 (40 p.p.m.) | 31.0 | 10.0 |
| (g) Copolymer 7/3 (40 p.p.m.) | 21.0 | 0 |
| (h) Copolymer 1/1 (1 × 10$^{-4}$) | 21.0 | 0 |
| (i) Copolymer 3/7 (40 p.p.m.) | 21.0 | 0 |
| (j) Copolymer G/L/T (32 p.p.m.) | 21.0 | 0 |
| (k) Glu/Tyr 1/1 (2 × 10$^{-4}$) | 18.0 | 0 |
| (l) Glu/Ala/Tyr 1/1/1 (32 p.p.m.) | 21.0 | 0 |
| (m) Tyr (32 p.p.m.) | 18.0 | 0 |

The copolymers tested as above indicated were prepared by copolymerization of alpha-amino acid anhydride mixtures by the procedure described in "Immunochemistry" supra. Copolymer 9/1, illustrative of the invention, was prepared from a 9:1 molar mixture of glutamic acid and tyrosine, and was determined by centrifugation to have a molecular weight of about 19,300. Copolymer 6/3/1, also illustrative of the invention, was prepared from a 6:3:1 molar mixture of glutamic acid, alanine and tyrosine, and was determined to have a molecular weight of about 90,800. The remaining copolymers are comparative. Thus, copolymers 7/3, 1/1 and 3/7 were prepared from mixtures containing proportions of glutamic acid: tyrosine outside those required herein, i.e. in molar ratios of 7:3, 1:1 and 3:7. Copolymer G/L/T was prepared from a 1:1:1 molar mixture of glutamic acid, lysine and tyrosine. The agents tested in (k), (l) and (m) were monomers or monomer mixtures including glutamic acid, tyrosine and/or alanine, the mixtures containing equal molar proportions of monomer components.

The results shown in TABLE I plainly show the effective inhibition by the copolymers of this invention, in (b), (c), (d), (e), and (f), of crystal growth of HAP in vitro, and that the inhibition is not due to complexation or chelation of calcium since sub-stoichiometric ratios of copolymer:calcium were employed. The failure of comparative agents (g) thru (m) to inhibit HAP formation emphasizes the criticality of the instant copolymers, with respect to components and ratios of such components therein, for achieving the unexpectedly improved HAP inhibition of this invention.

In the following examples illustrative of mouthwash formulations according to the invention, Pluronic F108 is a polyoxyalkylene block polymer.

| | Example | | | |
|---|---|---|---|---|
| | 2 | 3 | 4 | 5 |
| Flavor | 0.22% | 0.22% | 0.22% | 0.22% |
| Ethanol | 15.0 | 15.0 | 15.0 | 15.0 |
| Pluronic F108 | 3.0 | 3.0 | 3.0 | 3.0 |
| Glycerine | 10.0 | 10.0 | 10.0 | 10.0 |
| Na Saccharin | 0.03 | 0.03 | 0.03 | 0.03 |
| Copolymer 6/3/1 | 0.1 | 0.2 | 0.5 | 1.0 |
| Water q.s. to | 100 | 100 | 100 | 100 |

EXAMPLE 6

| Toothpaste Formulation | |
|---|---|
| | Wt. Percent |
| Glycerin | 25.0 |
| Carboxymethylcellulose | 1.3 |
| Sodium benzoate | 0.5 |
| Na Saccharin | 0.2 |
| Silica | 30.0 |
| Sodium lauryl sulfate | 1.5 |
| Flavor | 1.0 |
| Copolymer 9/1 | 3.0 |
| Water to make | 100 |

Thus invention has been disclosed with respect to preferred embodiments and it will be understood that modifications and variations thereof obvious to those skilled in the art are to be included within the spirit and preview of this application and the scope of the appended claims.

I claim:

1. An oral dentifrice toothpaste or mouthwash composition comprising an orally acceptable vehicle containing in an effective amount as an anticalculus agent a copolymer consisting essentially of (A) n units having the molecular configuration

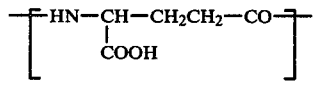

(B) m units having the molecular configuration

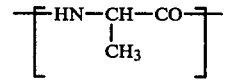

and (C) p units having the molecular configuration

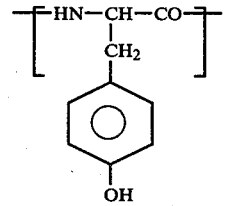

the ratio of (n+m):p ranging from about 5:1 to about 9.5:1 and the ratio of m:n ranging from 0:1 to about 0.6:1, the molecular weight of the copolymer ranging from about 5,000 to about 150,000.

2. An oral composition according to claim 1 wherein the ratio of n:m:p in the copolymer is about 9:0:1 and the copolymer has a molecular weight of about 17,000 to about 21,000.

3. An oral composition according to claim 1 wherein the ratio of n:m:p in the copolymer is about 6:3:1 and the copolymer has a molecular weight of about 80,000 to about 100,000.

4. The oral composition of claims 1, 2 or 3 containing about 0.01% to about 10% by weight of said copolymer.

5. The oral composition of claims 1, 2 or 3 containing about 0.5% to about 5% by weight of said copolymer.

6. The oral composition of claims 1, 2 or 3 which is a mouthwash having a pH of about 4.5 to about 9 and an aqueous-alcohol vehicle.

7. The oral composition of claims 1, 2 or 3 which is a toothpaste having a pH of about 4.5 to about 9, a liquid vehicle, a gelling agent and a dentally acceptable polishing agent.

8. A method of improving oral hygiene comprising applying an oral composition as defined in claims 1, 2 or 3 to said dental surfaces.

* * * * *